US00PP32413P2

(12) United States Plant Patent
Heuger

(10) Patent No.: US PP32,413 P2
(45) Date of Patent: Oct. 27, 2020

(54) ***HELLEBORUS* PLANT NAMED 'COSEH 7100'**

(50) Latin Name: ***Helleborus niger* X *Helleborus* x *hybridus***
Varietal Denomination: COSEH 7100

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,734

(22) Filed: Nov. 29, 2019

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 7100', characterized by its upright and mounded plant habit; moderately vigorous to vigorous growth habit; dark green-colored leaves; freely flowering habit; single red purple-colored flowers; and good garden performance.

2 Drawing Sheets

Figure 1:
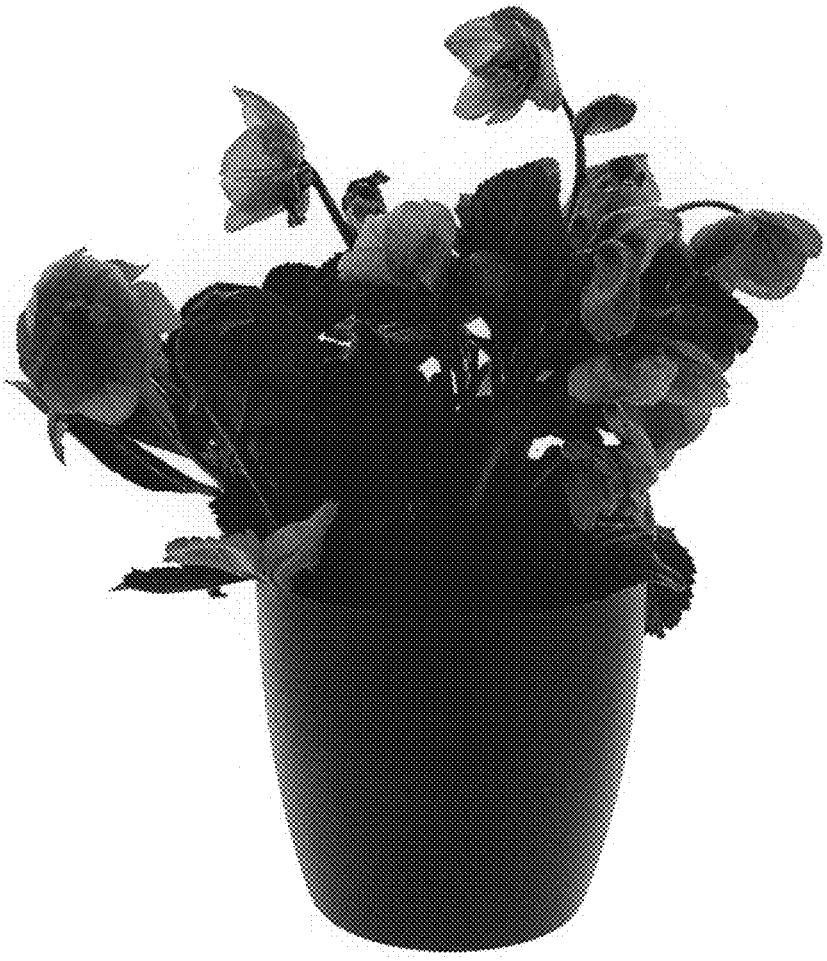

Botanical designation: *Helleborus niger* X *Helleborus* x *hybridus*.
Cultivar denomination: 'COSEH 7100'.

CROSS-REFERENCED TO CLOSELY-RELATED APPLICATIONS

Title: *Helleborus* Plant Named 'COSEH 5600'
Applicant: Josef Heuger
Plant patent application Ser. No. 16/602,791
Title: *Helleborus* Plant Named 'COSEH 5700'
Applicant: Josef Heuger
Plant patent application Ser. No. 16/602,738
Title: *Helleborus* Plant Named 'COSEH 5900'
Applicant: Josef Heuger
Plant patent application Ser. No. 16/602,735
Title: *Helleborus* Plant Named 'COSEH 6900'
Applicant: Josef Heuger
Filed: Concurrently with the instant application
Title: *Helleborus* Plant Named 'COSEH 7500'
Applicant: Josef Heuger
Plant patent application Ser. No. 16/602,736

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 7100'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a unnamed selection of *Helleborus niger*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by divisions in a controlled environment in Glandorf, Germany since February, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7100'. These characteristics in combination distinguish 'COSEH 7100' as a new and distinct *Helleborus* plant:

1. Upright and mounded plant habit.
2. Moderately vigorous to vigorous growth habit.
3. Dark green-colored leaves.
4. Freely flowering habit.
5. Single red purple-colored flowers.
6. Good garden performance.

Plants of the new *Helleborus* differ from plants of the female parent selection in the following characteristics:

1. Plants of the new *Helleborus* have larger flowers than plants of the female parent selection.
2. Plants of the new *Helleborus* have red purple-colored flowers whereas plants of the female parent selection have white-colored flowers.

Plants of the new *Helleborus* differ from plants of the male parent selection in the following characteristics:

1. Plants of the new *Helleborus* have fewer leaves than plants of the male parent selection.

2. Flowers of plants of the new *Helleborus* are red purple in color whereas flowers of plants of the male parent selection are dark red in color.

Plants of the new *Helleborus* can be compared to plants of *Helleborus niger* X *Helleborus* x *hybridus* 'COSEH 5600', disclosed in a U.S. Plant Patent application filed concurrently. Plants of the new *Helleborus* differ primarily from plants of 'COSEH 5600' in flower color as plants of the new *Helleborus* have red purple-colored flowers whereas plants of 'COSEH 5600' have yellow green, white and purple-colored flowers.

Plants of the new *Helleborus* can be compared to plants of *Helleborus niger* X *Helleborus* x *hybridus* 'COSEH 5700', disclosed in a U.S. Plant Patent application filed concurrently. Plants of the new *Helleborus* differ primarily from plants of 'COSEH 5700' in plant and growth habit as plants of the new *Helleborus* are not as compact as and are more vigorous than plants of 'COSEH 5700'.

Plants of the new *Helleborus* can be compared to plants of *Helleborus niger* X *Helleborus* x *hybridus* 'COSEH 5900', disclosed in a U.S. Plant Patent application filed concurrently. Plants of the new *Helleborus* differ primarily from plants of 'COSEH 5900' in flower color as plants of the new *Helleborus* have red purple-colored flowers whereas plants of 'COSEH 5900' have white-colored flowers.

Plants of the new *Helleborus* can be compared to plants of *Helleborus niger* X *Helleborus* x *hybridus* 'COSEH 6900', disclosed in a U.S. Plant Patent application filed concurrently. Plants of the new *Helleborus* differ primarily from plants of 'COSEH 6900' in flower color as plants of the new *Helleborus* have red purple-colored flowers whereas plants of 'COSEH 6900' have light yellow green-colored flowers.

Plants of the new *Helleborus* can be compared to plants of *Helleborus niger* X *Helleborus* x *hybridus* 'COSEH 7500', disclosed in a U.S. Plant Patent application filed concurrently. Plants of the new *Helleborus* differ primarily from plants of 'COSEH 7500' in flower color as plants of the new *Helleborus* have red purple-colored flowers whereas plants of 'COSEH 7500' have white to light yellow green-colored flowers.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Leaves of plants of the new *Helleborus* are lighter green in color than leaves of plants of 'LEM 100'.
2. Plants of the new *Helleborus* flower earlier than plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7100' grown in a container.

Figure 2:
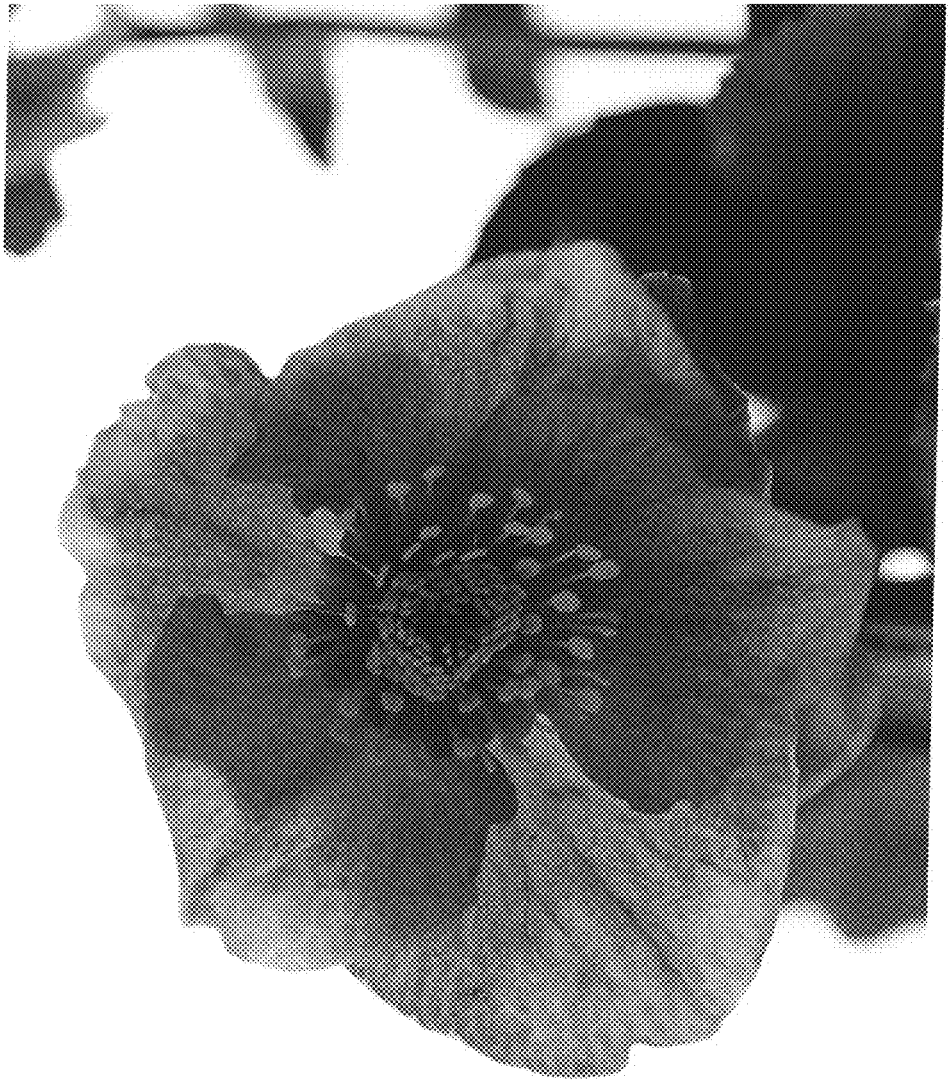

The photograph on the second sheet (FIG. 2 of 2) is a close-up view of a typical flower and leaves of 'COSEH 7100'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 7100'.

Parentage:

*Female, or seed, parent*.—Unnamed selection of *Helleborus niger*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous to vigorous growth habit and moderate growth rate.

*Plant height, soil level to top of foliar plane*.—About 23 cm.

*Plant height, soil level to top of flowers*.—About 29.5 cm.

*Plant diameter* (*area of spread*).—About 39.2 cm.

Leaf description:

*Arrangement*.—Leaves arranged in a basal rosette; leaves palmately compound with typically five leaflets per leaf.

*Leaf length*.—About 18.5 cm.

*Leaf width*.—About 22.2 cm.

*Leaflet length*.—About 12.1 cm.

*Leaflet width*.—About 8.7 cm.

*Leaf shape*.—Palmate; reniform in outline.

*Leaflet shape*.—Obovate to elliptic.

*Leaflet apex*.—Broadly acute.

*Leaflet base*.—Attenuate.

*Leaflet margin*.—Deeply serrate; slightly to moderately undulate.

*Leaflet texture and luster, upper surface*.—Smooth, glabrous; leathery; slightly glossy.

*Leaflet texture and luster, lower surface*.—Smooth, glabrous; leathery; very slightly glossy.

*Leaflet venation pattern*.—Pinnate.

*Leaflet color*.—Developing leaflets, upper surface: Close to 137A to 137B; midvein proximally, close to 187B. Developing leaflets, lower surface: Close to between 138B and 147B; midvein, close to 187B. Fully developed leaflets, upper surface: Darker than between NN137A and 147A; venation, close to 144B. Fully developed leaflets, lower surface: Close to 147B; venation, close to 144B.

*Petioles*.—Length: About 11 cm. Diameter: About 7 mm to 9 mm. Strength: Strong. Texture and luster, upper and lower surfaces: Smooth, glabrous; slightly glossy. Color, upper and lower surfaces: Close to 144A.

Flower description:

*Flower shape and habit*.—Single rotate flowers; flowers slightly cupped; arranged solitary or in clusters with about three flowers each; freely flowering habit with about 23 flowers developing per plant; flowers face mostly outwardly to slightly nodding.

*Fragrance*.—None detected.

*Natural flowering season*.—Plants begin flowering about ten months after planting; plants flower from the late autumn into the winter in Germany.

*Flower longevity on the plant*.—About ten days; sepals persistent, other flower parts are not persistent.

*Flower buds*.—Length: About 2.2 cm. Diameter: About 1.5 cm. Shape: Ovate. Texture and luster: Smooth, glabrous; matte. Color: Close to 157A; towards the apex and venation, close to 60C to 60D.

*Inflorescence height*.—About 7.9 cm.

*Inflorescence diameter*.—About 8.7 cm.

*Flower diameter*.—About 8.2 cm by 8.2 cm.

*Flower depth* (*height*).—About 3.3 cm.

*Petals*.—All petals are transformed into nectaries.

*Sepals*.—Quantity and arrangement: About five, arranged in a single whorl. Length: About 4.9 cm. Width: About 4.6 cm. Shape: Broadly ovate, slightly to moderately concave. Apex: Obtuse. Base: Truncate to rounded. Margin: Entire; not undulate. Texture and luster, upper and lower surfaces: Smooth, glabrous; matte. Color: When opening, upper surface: Slightly lighter than between 75C and 186D and heavily covered with fine dots, close to 64B; venation, similar to lamina color. When opening, lower surface: Close to 75C to slightly lighter than 75C and heavily covered with fine dots, close to 61A and 64A to 64B; venation, similar to lamina color. Fully opened, upper surface: Close to 76D and heavily covered with fine dots, close to 64B and 64C; venation, similar to lamina color; with development, close to 144A tinged with close to 186C and 186D. Fully opened, lower surface: Close to 75C, distally, close to 75D and heavily covered with fine dots, close to 64B and 64C; venation, close to 64B and 64C; with development, close to 183D tinged with close to 146C and venation, close to 187A.

*Flower bracts*.—Quantity per flower: Typically one or two. Length: About 4 cm. Width: About 3.1 cm. Shape: Broadly ovate. Apex: Acute. Base: Truncate. Margin: Finely serrate to serrate; not undulate. Color, upper surface: Close to between 139A and 147A; venation, similar to lamina. Color, lower surface: Close to 147B; venation, close to 183A.

*Peduncles*.—Length: About 18.8 cm. Diameter: About 5 mm to 7 mm. Aspect: About 20° from vertical. Strength: Strong. Texture and luster: Smooth, glabrous; slightly glossy. Color: Close to 145A and slightly covered with fine dots, close to 200C to 200D.

*Pedicels*.—Length: About 4.4 cm. Diameter: About 3.5 mm. Aspect: About 10° from peduncle axis. Strength: Moderately strong. Texture and luster: Smooth, glabrous; moderately glossy. Color: Close to 146C and heavily covered with fine dots, close to 183A.

*Reproductive organs*.—Stamens: Quantity per flower: About 120. Filament length: About 1.8 cm. Filament color: Close to NN155D. Anther shape: Double and broadly reniform; basifixed. Anther size: About 2 mm by 2 mm. Anther color: Close to 150C. Pollen amount: Moderate. Pollen color: Close to 4D. Pistils: Quantity per flower: About eight and occasionally, five to seven. Pistil length: About 7 mm. Stigma diameter: About 0.3 mm. Stigma shape: Club-shaped. Stigma color: Close to 150D. Style length: About 6.5 mm. Style color: Close to 59B to 59C. Ovary color: Close to 144C and towards the margins, close to 59D to lighter than 59D. Nectaries (transformed petals): Quantity per flower: About 16. Length: About 1.2 cm. Diameter: About 6 mm. Shape: Tubular, flattened. Texture and luster, inner and outer surfaces: Smooth, glabrous; slightly glossy. Color, immature, inner and outer surfaces: Close to 144C, distally, close to 145A and proximally, close to 200B. Color, mature, inner and outer surfaces: Close to 144C and proximally, close to 200A; with development, close to 144C, distally, close to 153D and proximally, close to 200C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7100' as illustrated and described.

* * * * *